United States Patent [19]

Kitado et al.

[11] Patent Number: 5,441,476
[45] Date of Patent: Aug. 15, 1995

[54] BODY TEMPERATURE REGULATION SYSTEM

[75] Inventors: Masako Kitado; Hiroyuki Inbe; Koichi Yoshida; Izumi Mihara, all of Kadoma, Japan

[73] Assignee: Matsushita Electric Works, Ltd., Osaka, Japan

[21] Appl. No.: 60,037

[22] Filed: May 11, 1993

[30] Foreign Application Priority Data

May 22, 1992 [JP] Japan .................................. 4-130716
Aug. 26, 1992 [JP] Japan .................................. 4-227597

[51] Int. Cl.⁶ ............................................ A61M 21/00
[52] U.S. Cl. ..................................... 600/26; 600/21; 128/736
[58] Field of Search .................................... 600/21–22, 600/26–28; 128/736

[56] References Cited

U.S. PATENT DOCUMENTS 4,034,740  7/1977  Atherton et al. ..................... 600/22
5,167,610 12/1992  Kitado et al. .

FOREIGN PATENT DOCUMENTS 60-101895  2/1985  Japan .
2299664    7/1990  Japan .
1232048    5/1971  United Kingdom ................. 600/22
2236190    3/1991  United Kingdom ................. 600/22

Primary Examiner—William E. Kamm
Assistant Examiner—John P. Lacyk
Attorney, Agent, or Firm—Leydig, Voit & Mayer

[57] ABSTRACT

A body temperature regulation system includes a discriminator which controls room temperature based on human body and room temperatures monitored by individual sensors. With this simple feedback system, the user can quickly fall asleep and reach a state of deep sleep.

17 Claims, 16 Drawing Sheets

BODY TEMPERATURE REGULATION SYSTEM

BACKGROUND OF THE INVENTION

This invention relates generally to a body temperature regulation system, and more particularly to a system for inducing a user's body temperature with a bed room environment adjusted so that a smooth falling asleep and a good quality sleeping can be assured.

DESCRIPTION OF RELATED ART

Accompanying social activities getting more complicated in recent years, such psychological and mental stresses as anxiety, dissatisfaction, anger, irritation and so on have been increased, and these stresses have been the cause for sleep disorders. Various attempts have been made to remove the stresses so as to quickly induce subjects into sleep stage and to keep them deeply asleep. In U.S. Pat. No. 5,167,610 to M. Kitado et al who are common to the present invention, for example, there has been suggested an apparatus for providing to users acoustic, vibratory and optical stimuli to an extent of giving them a pleasant feeling, and regulating room temperature or bed climate and room humidity also for giving to the users a pleasant feeling.

It is possible to adopt configulation for properly regulating the room temperature and humidity with an air conditioner with respect to the entire room atmosphere, as a known sleep inducing system, for the purpose of attaining the smooth falling asleep and good quality sleeping on the basis of the above information. For example, there can be executed such temperature and humidity regulation employing a socalled "good-night timer" incorporated in the air conditioner or, more specifically, a room temperature regulation for varying the temperature in accordance with the sleep by means of the air conditioner employing the "good-night timer", that is, properly increasing the room temperature after going to bed.

In Japanese Patent Laid-Open Publication No. 2-299664, further, there has been disclosed an arrangement in which a heat radiating plate consisting of a heat or cold storage member and capable of emitting a radiant heat is disposed on a side of bed for heating or cooling user's face and head. Further, there has been suggested an electric blanket provided with a heater circuit rendering generated heat to be the skin temperature of, for example, approximately 35° C. and in a range of ±0.5° C., while the temperature at such body part as toe, instep, leg, back, shoulder, hand and arm is used as the skin temperature, as seen for example in Japanese Patent Laid-Open Publication 60-101895.

On the other hand, it has been discovered by the present inventors as the result of eager research that, first, the sleep becomes deeper from the awakening state and, as sleep stage reaches St. 3, the temperature of skin surface becomes uniform, that is, the body temperature becomes substantially identical at any body parts, so as to be the socalled basal temperature (the state where the sleep becomes extremely deep and the basal temperature is attained shall be hereinafter referred to as "Slow Wave Sleep" or simply as "SWS"). Second, the basal temperature fluctuates in accordance with seasonal change in the atmospheric temperature, alike the basal metabolism, so as to be high in winter but to be low in summer. Third, taking this respect into account, the air or temperature conditioner (adapeted to the whole room space, to part of the room, or to both of them, and so on) is so controlled that skin surface temperature of the user body will quickly reach the basal temperature irrespective of the season, the user can be aided to fall asleep so as to quickly reach SWS.

Fourth, the most important skin temperature to the induction to falling asleep will be, among the skin surface temperature, at various points, leg temperatures (specifically the thighs temperature), which are heat radiating body parts of a large thermal capacity and a torso temperature including both arms and a facial temperature (specifically the forehead temperature). The face is closest to the brain, having the largest number of thermoreceptors, and most susceptible to variation in atmospheric environment as being exposed always to the atmosphere. Here, the head is a haired portion and has only few thermoreceptors. So, the head is improper for determining the sensitivity to heat/cool stimulus but, since the temperature regulatory center is in the brain, cooling a head will be effective to aid to fall asleep quickly. In these respects, the induction to falling asleep can be aided by keeping the leg including the thighs and the torso including the arms not to be cooled but rather warmed, preferably, while cooling the head, and the basal temperature can be quickly reached. Fifth, it is desired that length of time from bedtime to the onset deep sleep (SWS) be decreased, when the sleep is not in a state deeper than the deep sleep of SWS, the user is likely to be awakened by any noise or light so as to repeat awakening and sleep stages and, consequently, it requires many hours until the deep sleep is reached. Here, in the event where the deep sleep stage of SWS cannot be reached, the fatigue relieving efficiency is decreased and the metabolism cannot be sufficiently decreased, and it becomes extremely difficult to save a large energy required for maintaining the homeostasis due to that the human being is one of homeotherm.

Sixth, when, not only the skin surface temperature, any difference between the core temperature and the skin temperature of the body is made small, the temperatures at core and surface portions can be made uniform, and the falling asleep (the term until the deep sleep SWS is reached) can be aided by controlling the air or temperature conditioner (the one adapted either to the whole room space, part of the room space or both) and so on so as to quickly attain the basal temperature. Seventh, the relative humidity in the room does not constitute such large thermal environmental factor as the temperature determinative to the falling asleep speed, but the humidity should preferably be approximately 50 to 65% throughout four seasons. The humidity is high in the temperature dependence, and is contributive to aid to fall asleep when the humidity is low in the event where the room temperature in higher (when, for example, the room temperature is approximately 28° C., the relative humidity is approximately 50%).

In the case of such "good-night timer" of the air conditioner as has been described, the conditioner is to be only calculated at a fixed temperature state once after the temperature is increased to a certain extent after the user goes to the bed, so that there may arise a problem that the user's body is cooled excessively in the deep sleep period SWS in which body temperature regulatory function does not work or in a socalled rapid eye movement (REM) period in which autonomic nervous system is distracted, or such inadequate temperature as an excessively high or low temperature occurs so as to cause an intermediate awakening state to appear. Even in the case of the falling asleep induction device in which the heat radiating plate constituted by the heat or cold storage material which can emit radiant heat is placed at the user's bedside so as to radiate a hot or cold air towards the user's head and face, the temperature is kept constant or to be gradually increased at dawn and the heat radiating plate constituted by the heat or cold storage material is extremely difficult to be controlled for increasing the temperature, so that there may arise the similar problem of the excessive cooling or the intermediate awakening in the deep or REM sleep period, to the foregoing case employing the air conditioner. In either one of these two, the temperature control is performed on the basis of a predetermined time schedule, irrespective of the body temperature condition of the user upon going to the bed, that is, whether or not the user's body is cold, and it is not always that the optimum control is performed during the sleeping in which the body temperature regulatory function does not work. Further, in the event where only the air conditioner adapted to regulate the temperature of the whole room space on the basis of the information on the skin surface temperature detected as, in particular, the facial temperature and the let temperature including that of the thighs, it is impossible to heat or cool any specific portion of the body, and there arises a problem that a suitable skin temperature distribution state for aiding the falling asleep with the let (specifically the thighs) generally of a lower temperature warmed up but with the face generally of a higher temperature cooled down cannot be created without an extreme difficulty, and the function of the falling asleep is decreased.

Further, in the case of such sleeping heater as the electric blanket having the heater circuit adapted to control the skin temperature at the toe, instep, leg, back, shoulder, hand or arm to be at approximately 35° C. with the tolerance of ±0.5° C., it is intended to keep the skin temperature uniformly at approximately 35 ±0.5° C. irrespective of that the skin temperature suitable for the falling asleep should differ depending on the body part, so that there may arise a problem that the effect of the thus controlled heating is likely to be insufficient and is even decreased due to the absence of any means for providing to the face any cold air. The facial temperature corresponds excellently to any change in the brain temperature which decreases the set point of the body temperature for the purpose of decreasing the metabolism, and it has been found that the brain temperature itself is decreased by approximately 0.5 to 1.0° C. after going to the bed in winter time. Further, in the case when the skin temperature is to be detected at such body part as the toe or instep, the skin temperature is influenced extremely sharply by the environment so that the skin temperature will be immediately decreased when, for example, the user's feet are out of the blanket after turning in the bed or the user has been in bare feet immediately before going to the bed, the extent of such influenced temperature range is quite remarkable, some user may easily fall asleep at normal rate even when the leg skin temperature is low, and there arises a problem that the leg is not suitable for detecting the skin temperature for use in controlling the sleeping heater or air conditioner. It has been also found that in the season when the electric blanket is suitably employable the skin temperature is also lower than in other seasons, and the controlling temperature is not required to be limited to the foregoing value 35±0.5° C. but is required to be within a somewhat broader temperature range of, for example, 34° to 36° C.

SUMMARY OF THE INVENTION

A primary object of the present invention is, therefore, to provide a body temperature regulation system capable of quickly leading the user's body temperature to the basal temperature and effectively contributive to the induction of the user into the deep sleep stage of SWS.

Another object of the present invention is to provide a body temperature regulation system which can lead the user quickly to the basal temperature in accordance with seasonal fluctuation and can be effectively contributive to the induction of the user into the deep sleep stage of SWS.

A further object of the present invention is to provide a body temperature regulation system which can render the body temperature to be uniform throughout core and surface portions with any difference between the core temperature and the skin temperature minimized, so as to quickly lead the user to the basal temperature, and thus can be effective contributive to the induction of the user to the deep sleep stage of SWS.

Still another object of the present invention is to provide a body temperature regulation system which can excellently set the relative surrounding humidity of the user in correspondence to environmental factors for the temperature, so as to render the falling asleep to be remarkably effective.

All other objects and advantages of the present invention shall become clear when following description of the invention detailed with reference to embodiments shown in accompanying drawings advances.

While the present invention shall be described in the followings with reference to the respective embodiments shown in the accompanying drawings, it will be appreciated that the intention is not to limit the invention only to these embodiments but rather to include all alterations, modifications and equivalent arrangements possible within the scope of appended claims.

DETAILED DESCRIPTION OF THE PREFERRED EMBODIMENTS

Figure 1:
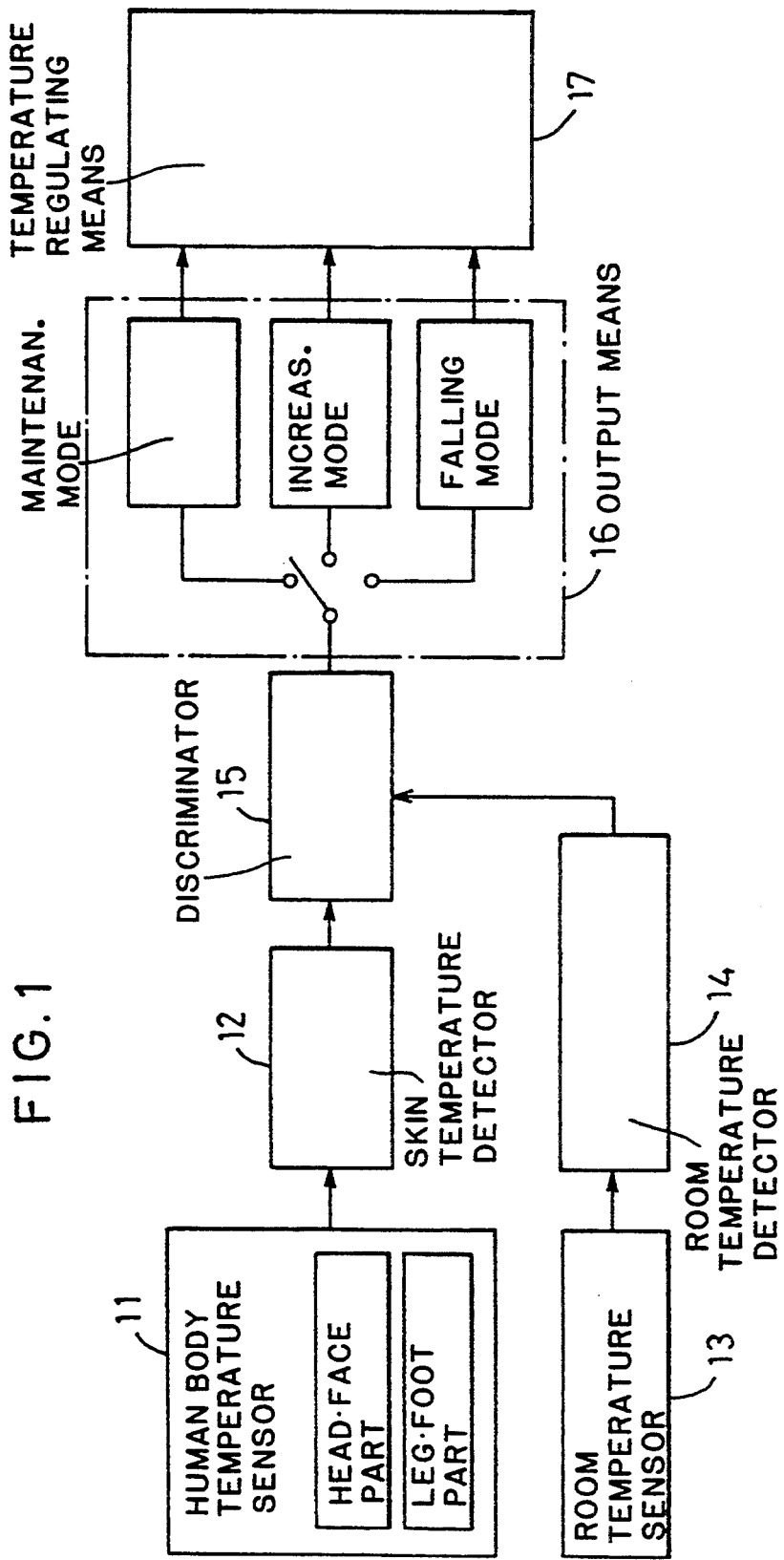
FIG. 1 shows in a block diagram an embodiment of the body temperature regulation system according to the present invention.

Referring first to FIG. 1 showing an embodiment of the body temperature regulation system according to the present invention, this system comprises a human body temperature sensor 11 for detecting the skin temperature of the user with such temperature detector as a thermistor, thermocouple, infrared ray sensor or the like, which sensor 11 is used to measure the skin surface temperature of user at such parts as the face (specifically the forehead), the leg (specifically the thighs) and the like. An output signal of this temperature sensor 11 is provided to a skin temperature detector 12, where the temperature at the face (specifically the forehead) and the leg (specifically the thighs) are detected. The system further comprises a room temperature sensor 13 employing also such temperature detector as the thermistor, thermocouple, infrared ray sensor or the like. An output signal of this room temperature sensor 13 is provided to a room temperature detector 14 which provides its output signal to a discriminator 15 together with an output signal of the skin temperature detector 12, and a temperature control mode is determined in the discriminator 15 on the basis of these output signals received. In this case, it is also possible to employ, instead of the room temperature sensor 13 and a room temperature detector 14, a regional temperature sensor adapted to sense the temperature at a local part of the room near a bed as the surrounding temperature, as well as a regional temperature detecting means.

Figure 2:
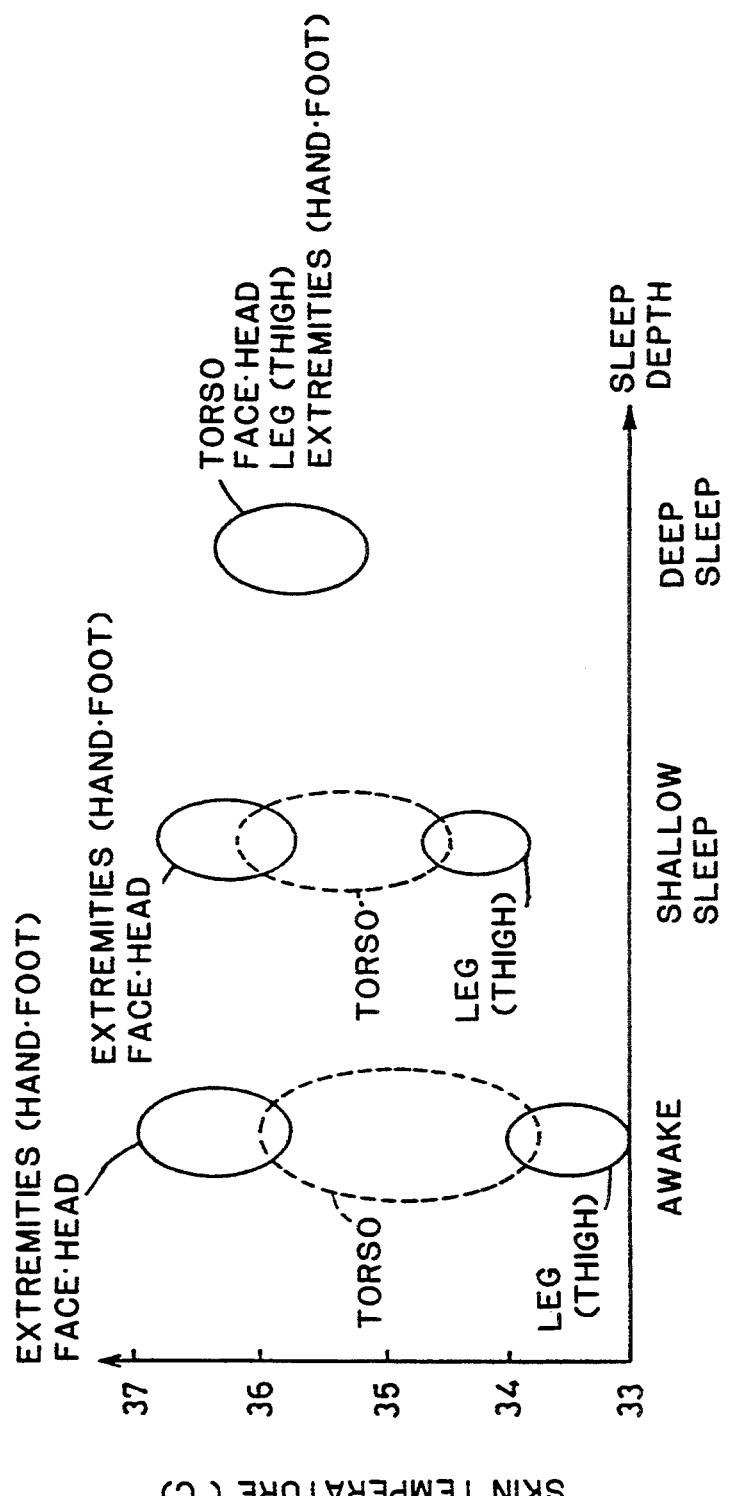
FIG. 2 is an explanatory diagram for the relationship between the sleep depth and the skin temperature.

Now, a case of a person having a body temperature of 36.5° C. shall be described as an example. In FIG. 2, the relation, in summer, between sleep depth and skin temperature, i.e., body surface temperature is shown. The respective temperatures detected at the respective body parts involve a large temperature difference lying in a range of approximately 33° to 37° C. during wakefulness, such that the leg temperature (specifically the thighs temperature) is at the bottom of the range and the temperature of the face or such extremities as hands and fingers are at the top of the temperature range. The torso temperature should be approximately in the center of the temperature range. As the sleep becomes deeper, the difference of the respective temperatures decreases so that, at a shallow sleep state (also referred to as "shallow sleep"), defined as St. 1 sleep or St. 2 sleep, the leg temperature increases to render the temperature difference within a range of approximately 3° C. In a deep sleep state, defined as St. 3 sleep or St. 4 sleep (also referred to as "deep sleep" or "SWS"), the respective temperatures of the different parts, excluding extremeties, converge to an extremely narrow range of approximately 35° to 36.5° C., and including extremities converge to approximately 35° to 37° C. Accordingly, the discriminator 15 determines the control mode on the basis of the detected temperature at the respective parts of the user, and previous the control mode signal to an output means 16. Firstly, in an event where the leg temperature (specifically the thigh temperature) is low and the facial temperature (specifically the forehead temperature) lies within the full range (33° C. to 37° C.), the control mode is set an increasing mode. In an event when the leg temperature (specifically the thigh temperature) is high and the facial temperature is in a range from an intermediate temperature to a high temperature, the control mode is set to a falling mode. When the leg temperature is in adequate range for deep sleep (35° C. to 37° C.), temperature lies within the full range, then the control mode is set to a maintenance mode (maintaining current temperatures).

From the output means 16, a signal of the proper control mode is provided to a temperature regulating means 17 for controlling body temperatures (e.g., an air conditioner in the present embodiment), in response to the output of the discriminator 15. At the time of going to bed, in particular, upon falling asleep, leg and facial temperatures are monitored with the leg temperature, which tends to decrease, given a greater weight. When the leg temperature is lower than the converging temperature range in the deep sleep state as shown in FIG. 2, the control will be executed with the operating mode set to a slight temperature increasing mode. When the leg and facial temperatures are both high, the control mode will be executed with the operating mode set to a slight decreasing mode. When the leg temperature is in an adequate range, the operating mode is set to a maintenance mode. With an air conditioner or other general cooling/heating devices as the main temperature regulating means, radiative cooling and heating devices for the user's face may be employed. The air conditioner is not be required to be limited only to the whole room type, but can also be adapted to a regional part of the room. Further, a device which can directly or indirectly cool or heat more than two parts of the head, body and legs, with air vents incorporating a temperature difference provided by a microcomputer controlled circuit, timer, etc., may also be usefully employed. Important here is that a temperature regulating means employed will realize an operating mode of cooling the face (specifically the forehead) when at least the leg (specifically the thighs) are in a range from a proper temperature to a high temperature.

Figure 3:
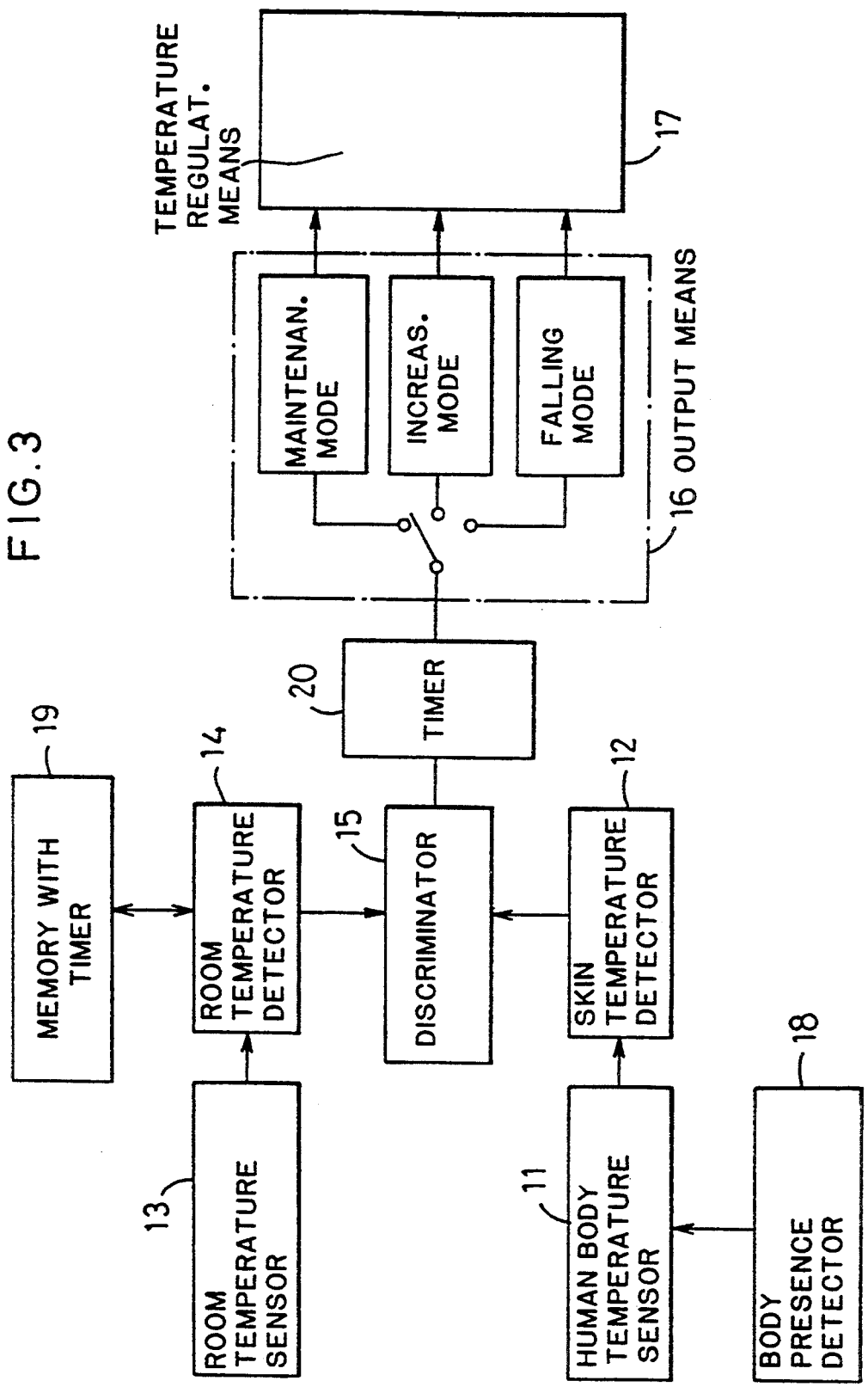
FIG. 3 shows in a block diagram another embodiment of the present invention.
Figure 4A:
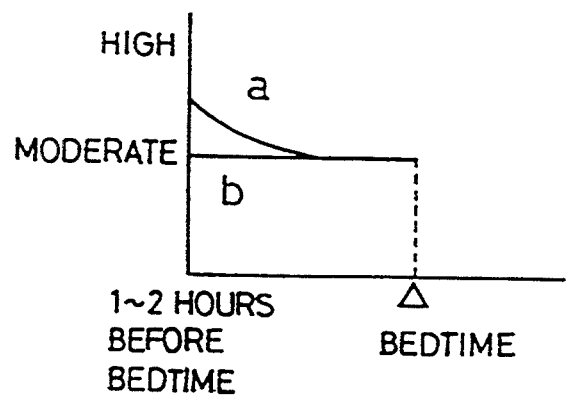
FIGS. 4A and 4B are explanatory diagrams for the variation in the room temperature with time until going into bed, in the system of the present invention and in known devices.
Figure 4B:
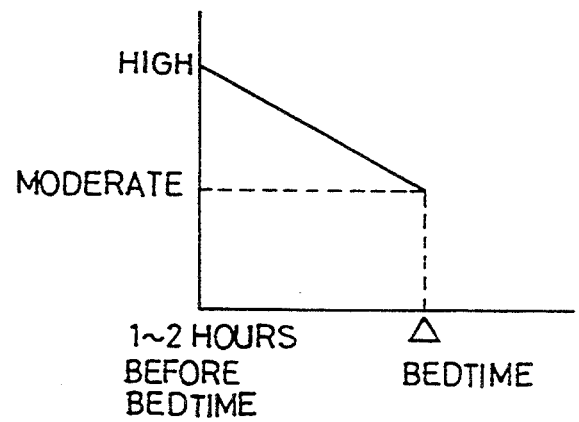
Figure 5:
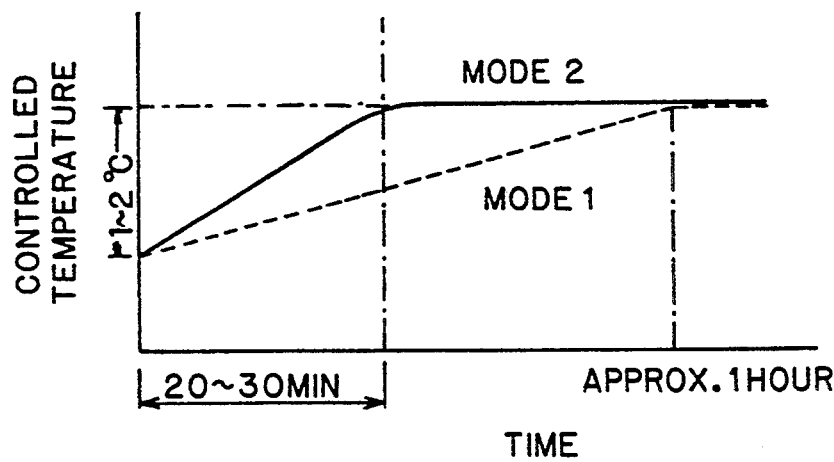
FIG. 5 is an explanatory diagram for sleep modes in the embodiment of FIG. 3.

In another embodiment according to the present invention as shown in FIG. 3, the same constituents as those in the embodiment of FIG. 1 are shown with the same reference numerals, a memory 19 with a timer is connected to the room temperature detector 14. The temperature data constantly gathered and stored in the memory 19 for a period one to two hours prior to switching to "fall asleep" mode. When temperature data acquisition commences, another timer, "Goodnight timer", activates. All events occurring during the subsequent sleep session are relative in time to the activation of the "Good-night timer". The human body temperature sensor 11 includes a body presence detecor 18, so that the discriminator 15 determines a temperature pattern for a time immediately after switching to fall asleep mode, dependent upon the length of time for which the user has been in the bedroom, the skin temperature value of the user, and the temperature variation of the bedroom. Thus, as shown in FIG. 4A, a relatively gradual temperature decreasing mode is carried out from a time one to two hours before going to bed. As shown in FIG. 4B, a linear temperature decreasing mode may be carried out by means of a unique control method. As shown in FIG. 5, the temperature regulating means 17 is so controlled by "Good-night timer" that, when the room temperature has been decreased from a higher temperature to an adequate temperature, and the user's body temperature is not excessively decreased, the room temperature will be increased relatively slowly, reaching a steady-state condition after approximately one hour, when the skin temperature is low, the temperature will be increased relatively quickly, reaching a steady-state condition after approximately 20 to 30 minutes. For example, the extent of the temperature increase, while it may be varied as occasion demands, 1° to 2° C. when the user has the body temperature of approximately 36.5° C.

Figure 6:
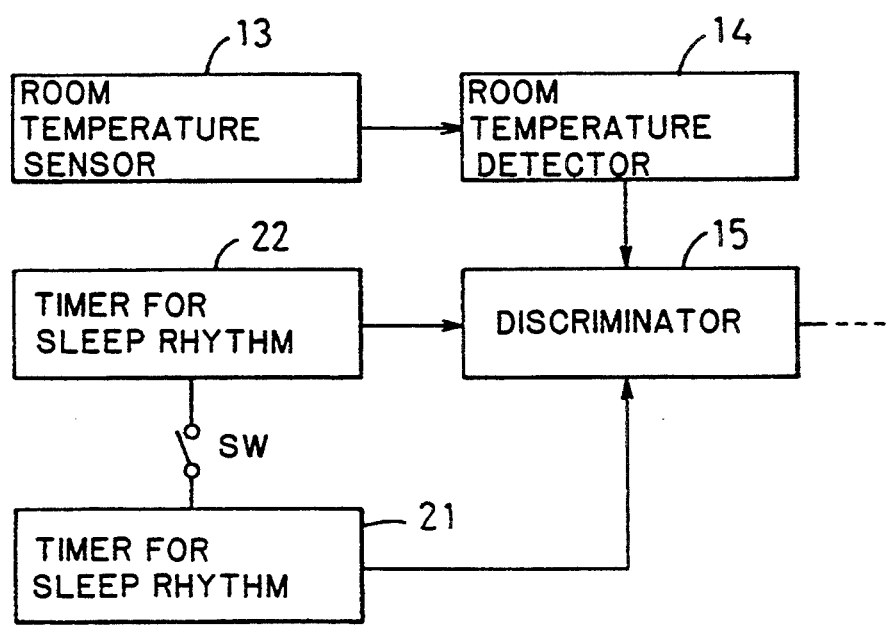
FIG. 6 shows in a block diagram another embodiment of the present invention.
Figure 9:
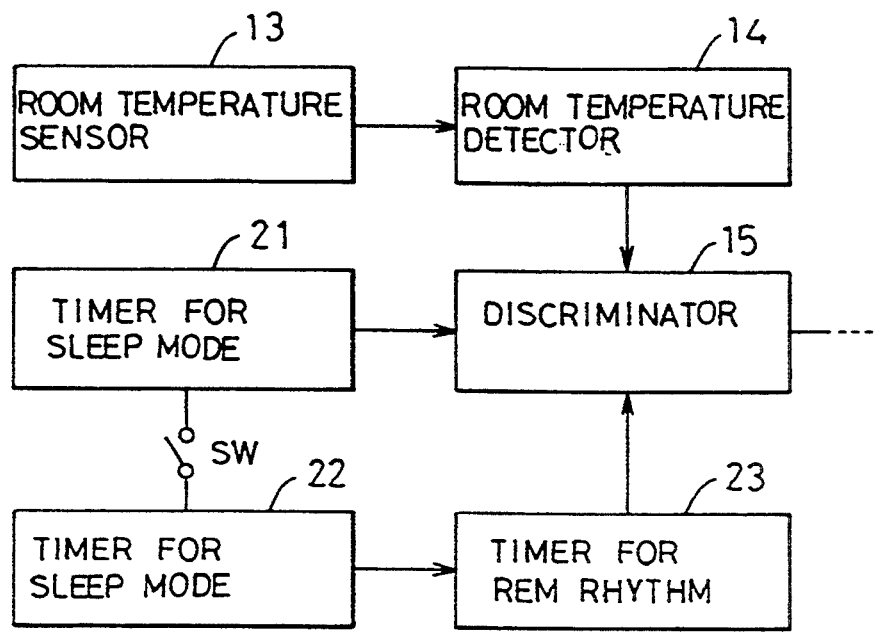
FIGS. 9 and 10 are block diagrams showing further embodiments according to the present invention.
Figure 10:
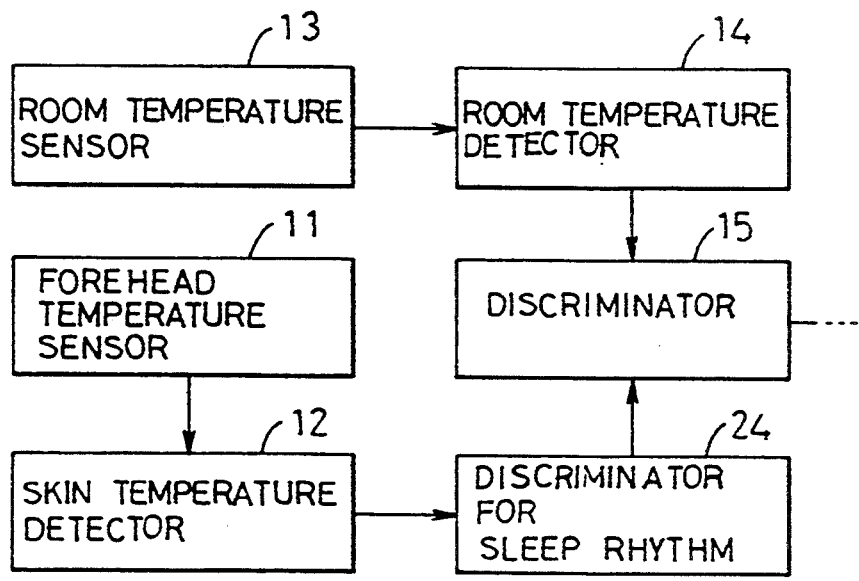

In another embodiment shown in FIG. 6 and modifications thereof shown in FIGS. 9 and 10, the same constituents as those in the embodiment of FIG. 1 are denoted by the same reference numerals.

Figure 7:
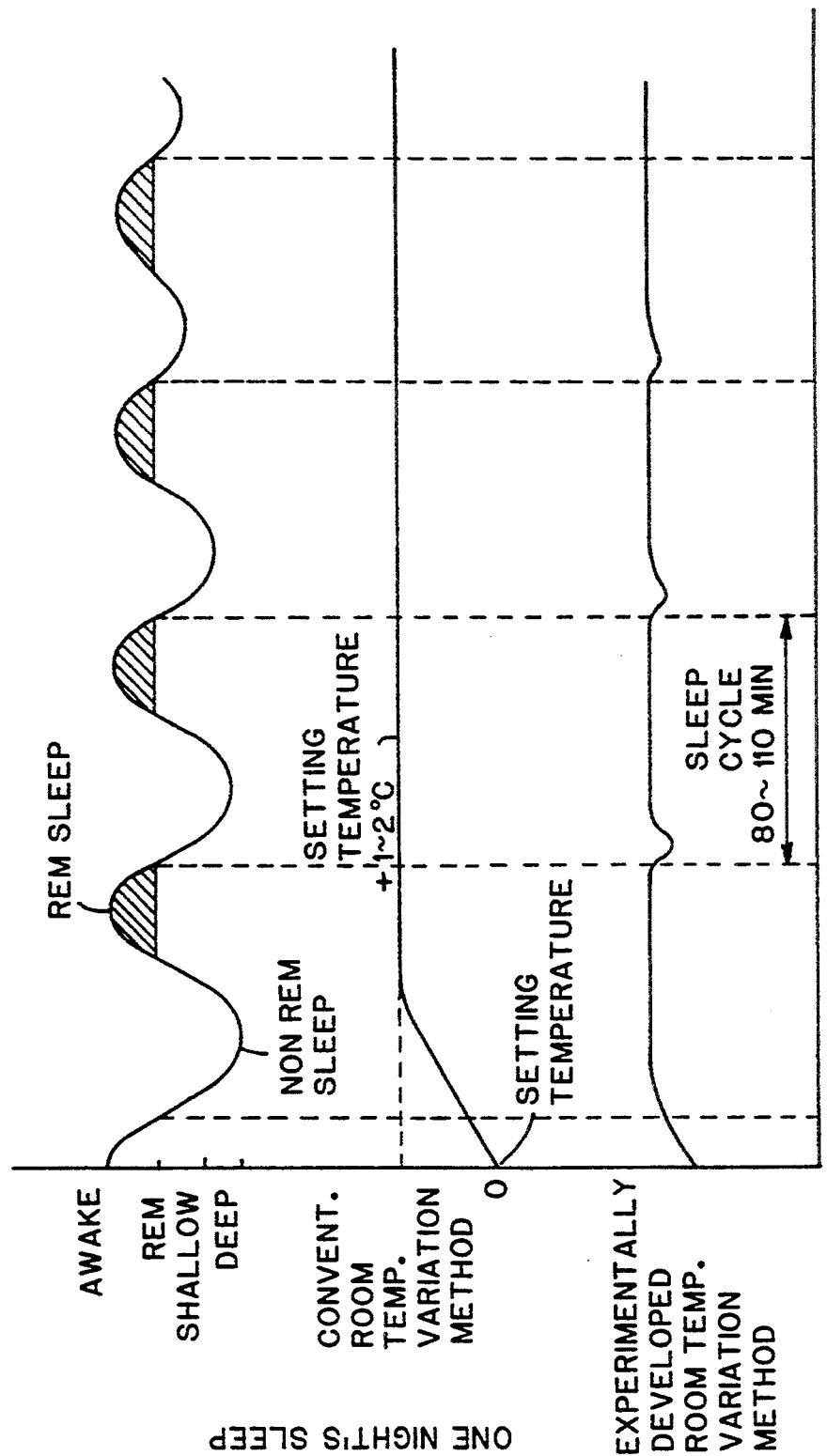
FIG. 7 is an explanatory diagram for the controlling operation suitable for a sleep rhythm according to the embodiment of FIG. 6.
Figure 8:
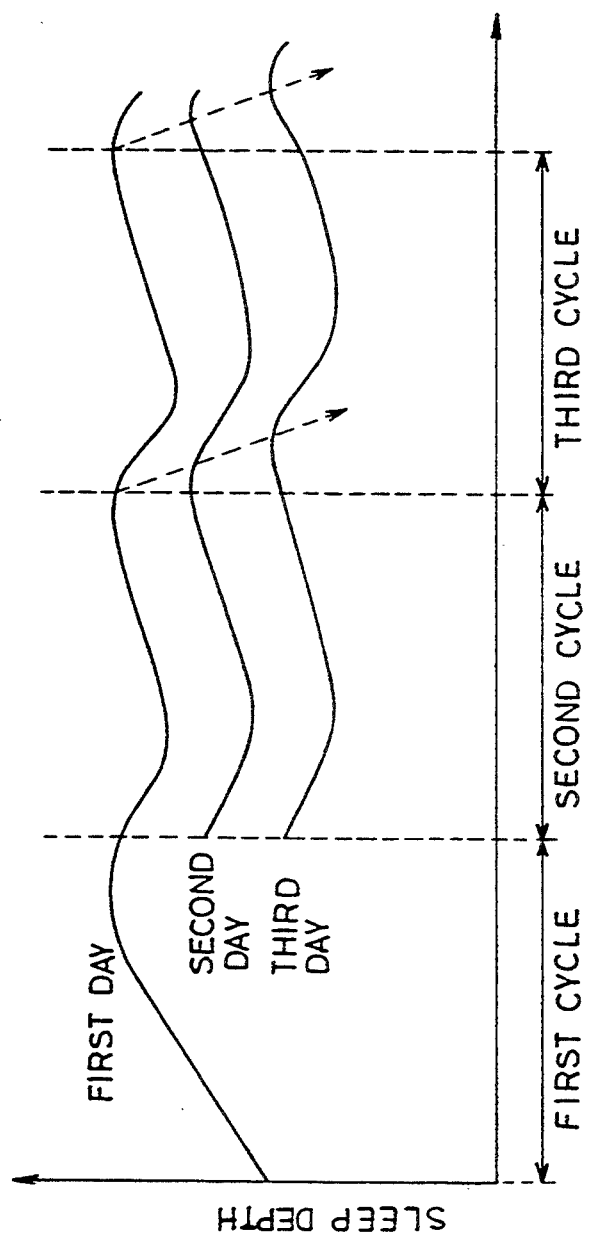
FIG. 8 is an explanatory diagram for the controlling operation corresponding to a delay in the REM sleep rhythm along the embodiment of FIG. 6.

In the embodiment shown in FIG. 6, the temperature is controlled so that varies synchronized with a sleep rhythm (REM-NREM cycle). In the present instance, there are provided a sleep mode timer 21, which actuates upon falling asleep, for increasing the room temperature, and a sleep rhythm timer 22 connected through a switch SW to the sleep mode timer 21. After the room temperature reaches a steady-state condition, the switch SW will close, changing the timer to the sleep rhythm timer 22, which measures the depth of sleep, thus synchronizing the temperature regulating device with the sleep rhythm. In this embodiment, as shown in FIG. 7 following the actuation of the sleep rhythm timer 22 (initiation of the sleep mode), from the end of the REM sleep in the first cycle the temperature is slightly decreased, the temperature is gradually increased from a time slightly before the transition from shallow sleep to deep sleep, to the end of the following REM sleep period. Following the end of each REM-sleep period, the room temperature is decreased until the onset of deep sleep, at which time, the temperature is increased until it reaches the original steady-state condition. Such temperature decreasing and increasing are repeated every sleep cycle of the sleep mode. For example, each sleep cycle lasts 80 to 110 minutes, and the air conditioning is optimumly controlled, repeatedly, by the output signal of the sleep rhythm timer 22. The onset time of the REM sleep periods deviate slightly from day to day, as shown in FIG. 8. This deviation is rhythmic with a period of approximately half of a 15 days. Optimumly, a REM rhythm timer 23 is connected to the discriminator 15 and sleep rhythm timer 22 as shown in FIG. 9, so that a phase deviation (delay) will occur in the temperature variation pattern for every cycle, and the phase difference of every day will thereby be removed.

Figure 19:
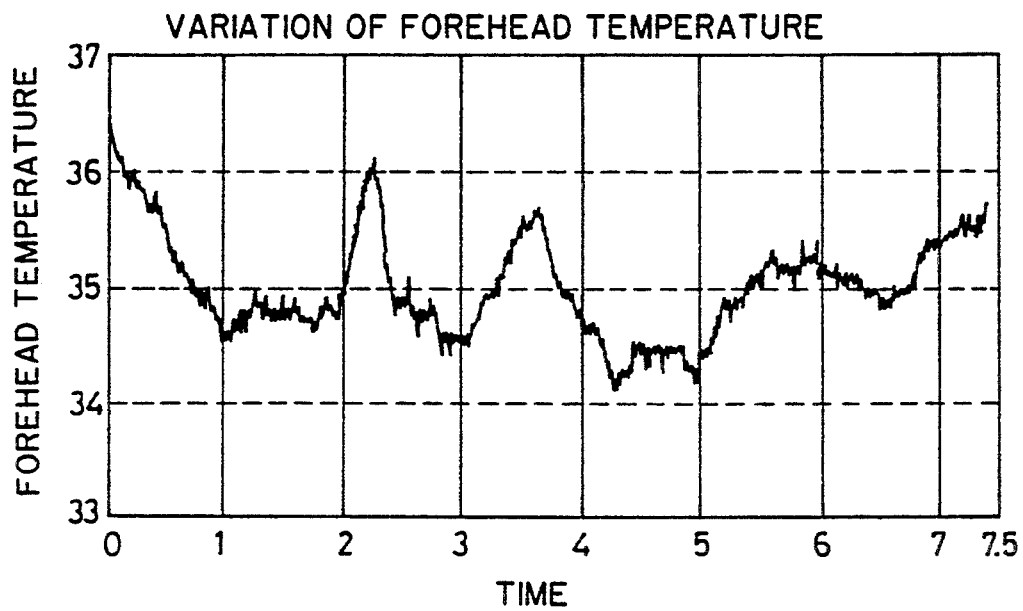
FIGS. 19 and 20 are explanatory diagrams for the relationship respectively of the facial temperature (specifically the forehead temperature) and the sleep stage to the time.
Figure 20:
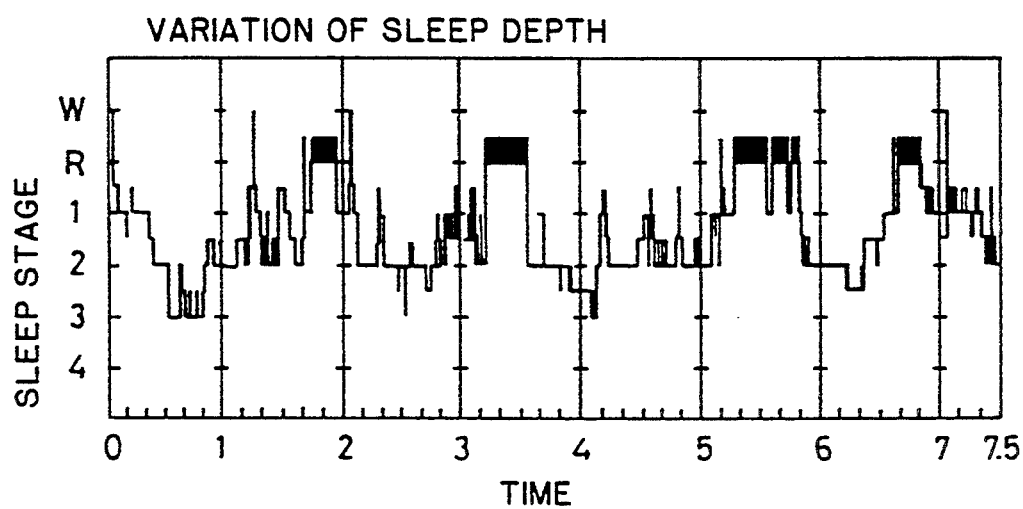

Furthermore, facial temperature (specifically the forehead temperature) and sleep depth are highly correlated as shown in FIGS. 19 and 20. Sleep rhythm can be determined from the facial temperature (specifically the forehead temperature) data.

As shown in FIG. 10, a sleep rhythm discriminator 24 for calculating and determining the sleep rhythm from the facial temperature (specifically the forehead temperature) is connected to the discriminator 15 and skin temperature detector 12. The output signals from the sleep rhythm discriminator 24 is fed back to the discriminator 15 for controlling the room temperature. The facial temperature (specifically the forehead temperature) causes a phase deviation of 10 to 20 minutes with respect to the sleep rhythm, but this phase deviation can be effectively conpensated for.

Figure 11:
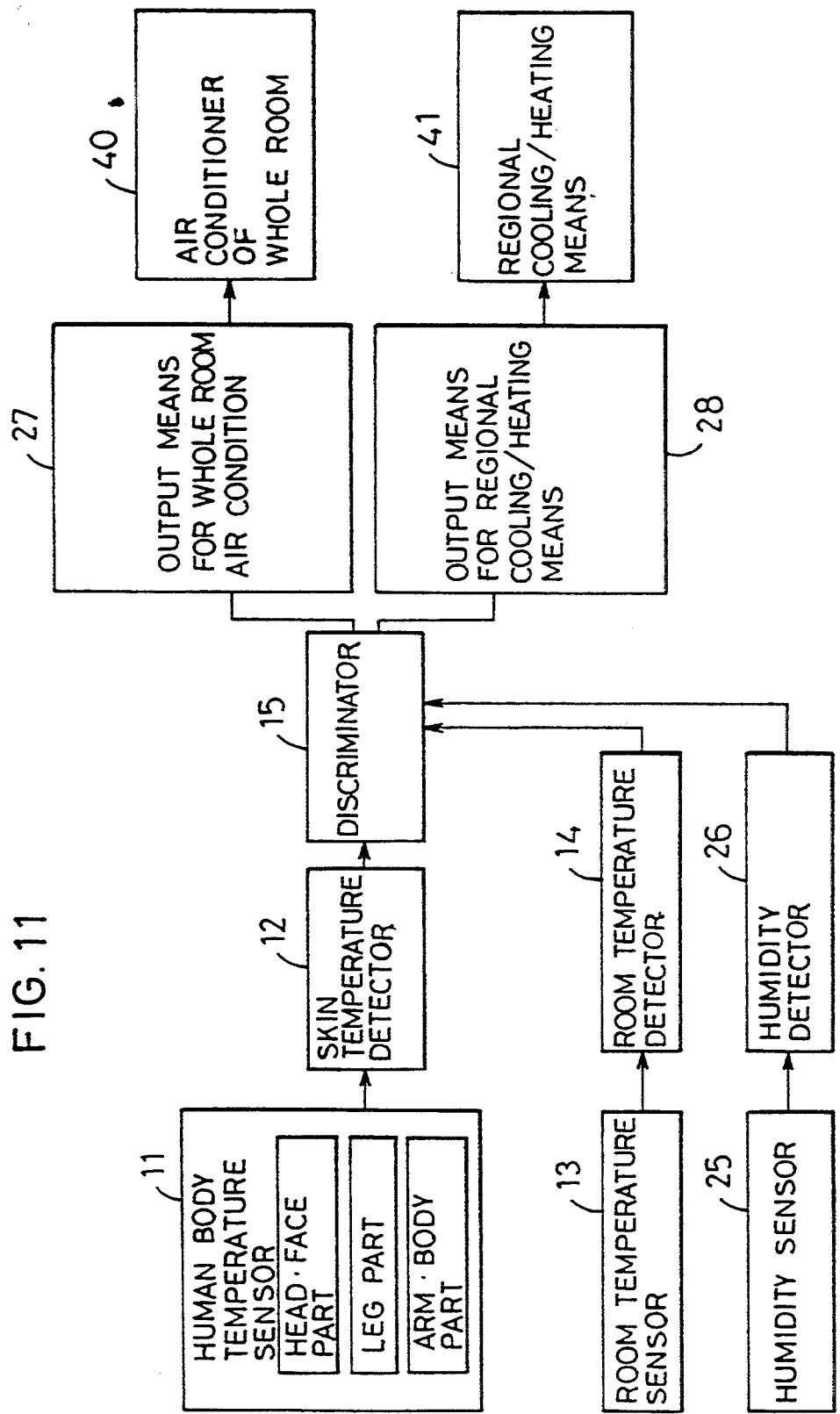
FIG. 11 is a block diagram showing still another embodiment according to the present invention.
Figure 16:
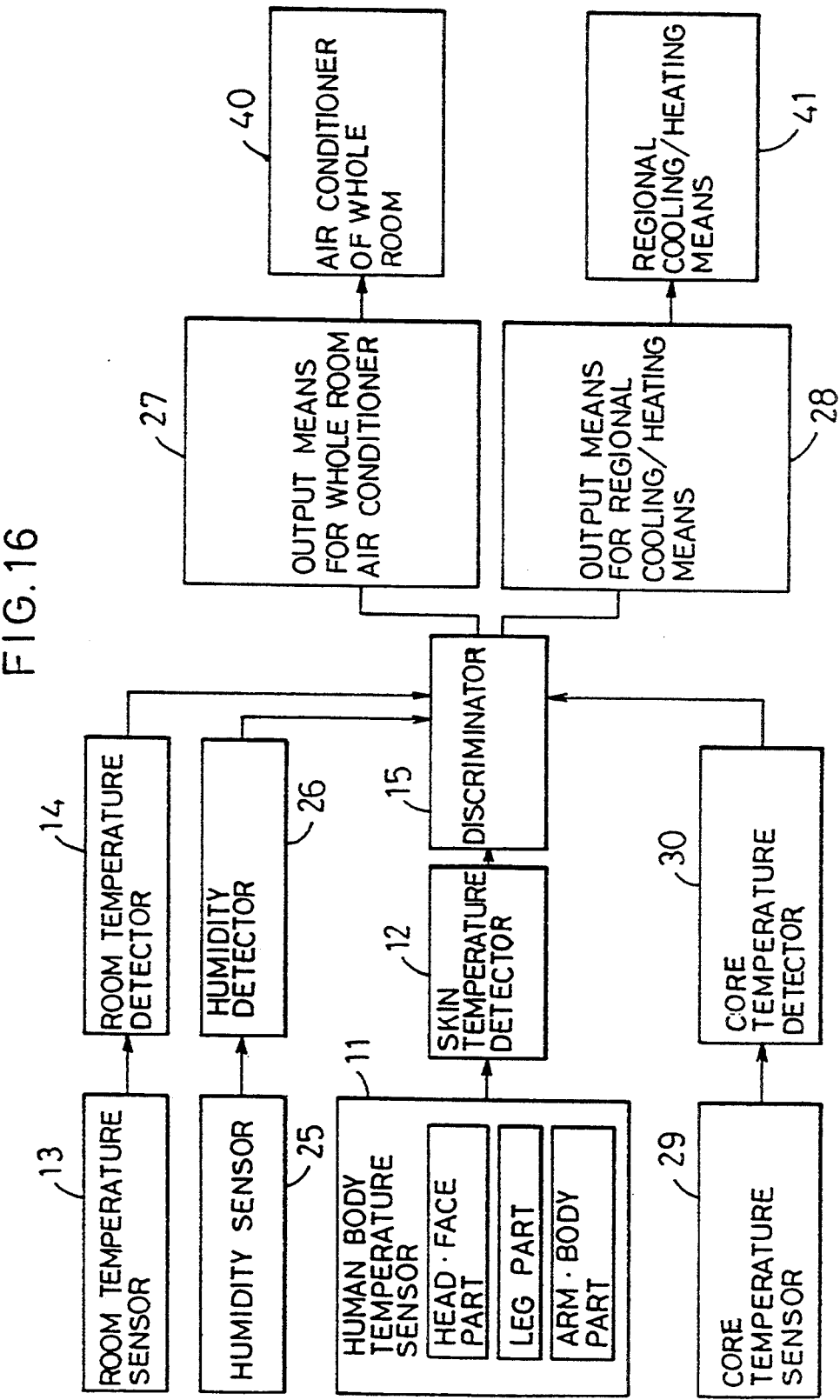
FIGS. 16 to 18 are block diagrams showing still further embodiments according to the present invention.

In another embodiments shown in FIGS. 11 and 16, the same constituents as those in the embodiment of FIG. 1 are denoted by the same reference numerals.

Figure 12:
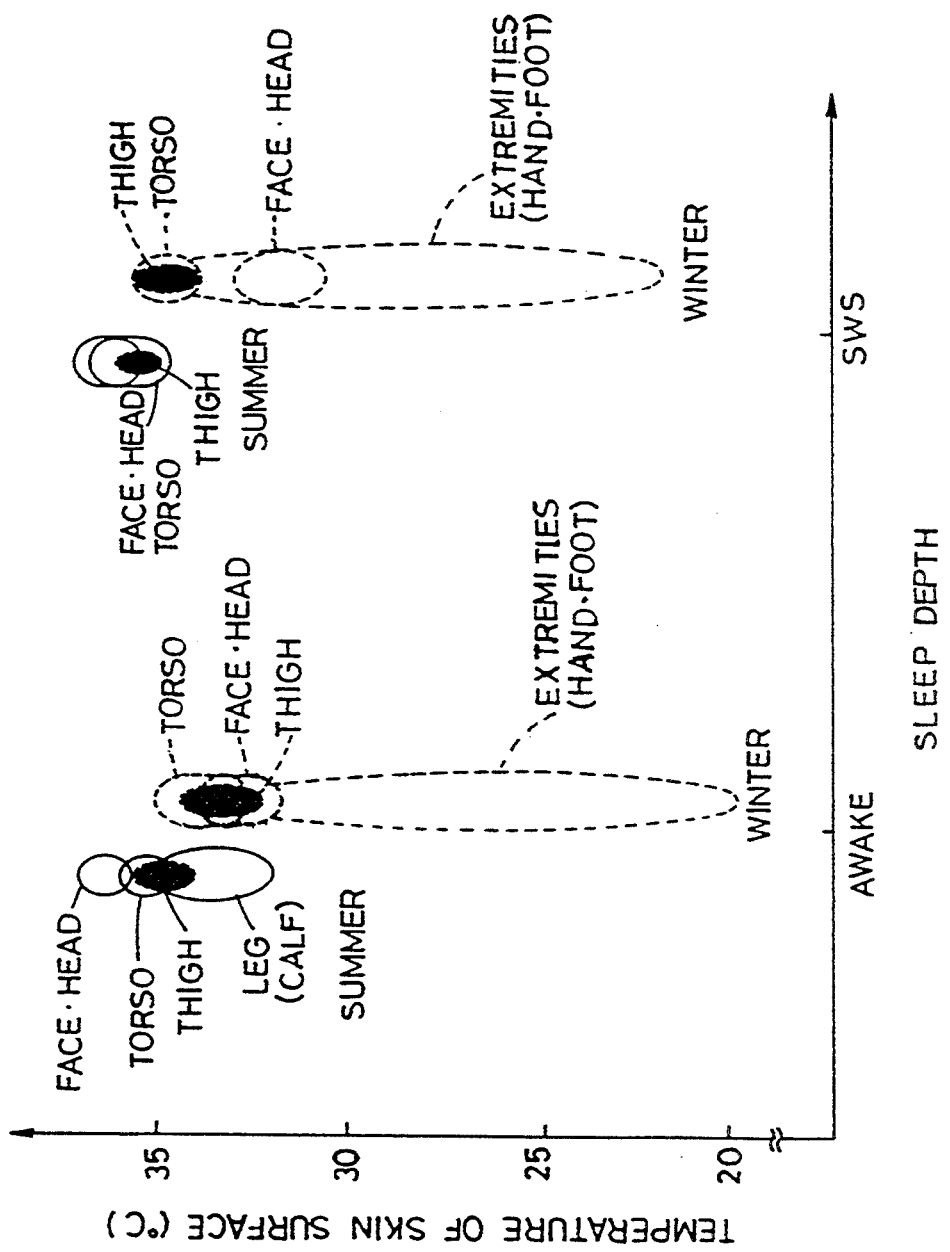
FIG. 12 is a diagram showing the relationship between the sleep stage and the skin surface temperature in the embodiment of FIG. 11.

In the embodiment shown in FIG. 11, a humidity sensor 25 is provided for effectively detecting the humidity within the room. The output signal of this humidity sensor 25 is connected to a humidity detector 26. The output signal of the humidity detector 26 is connected with the output signals of the room temperature detector 14 and skin temperature detector 12 to the discriminator 15. The temperature control mode is determined on the basis of the information given by the signals from the skin temperature detector 12, the room temperature detector 14 and the humidity detector 26. During sleep in the steady-state condition the relative humidity is regulated within a range of 50 to 65%. The relationship between the sleep depth and the skin surface temperature in summer and winter (including late autumn) are shown in FIG. 12. The relationship in season is as that which has been partly described in FIG. 2. The relationship in winter shows that, while awake, torso, leg and extremities temperatures are much lower than the respective temperatures during winter, but during deep sleep, they are slightly increased (though they are all lower than those in the summer due to influence of circumferential temperature) except for the facial temperature (specifically the forehead temperature), which is slightly decreased, hence, the temperature distribution decreases. In all seasons, the torso and leg temperatures (body parts which are covered) are less influenced by the room temperature; therefore, the difference between the torso and leg temperatures will decrease from wakefulness to deep sleep.

Figure 13:
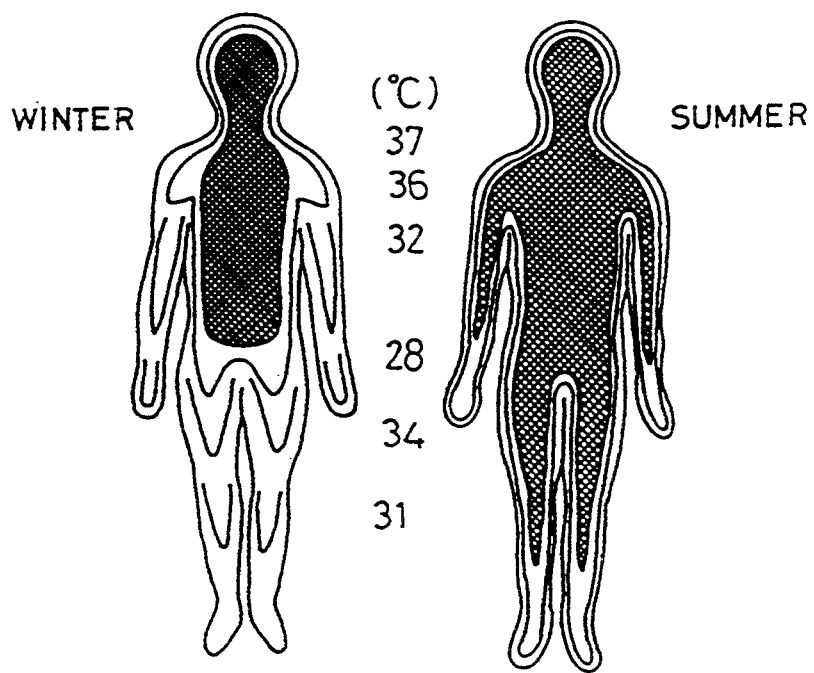
FIG. 13 is a diagram showing body temperature distributions under cold and hot environments.

In general, there are seasonal body temperature differences in both core temperatures and surface temperatures, as shown in FIG. 13. Under such a warm condition of summer as shown in the right side illustration, the higher temperature zone expands to increase the body surface temperature. Under such a cool condition of winter, as shown in the left side illustration, the higher temperature zone reduces so that body parts of smaller heat capacity (arms and legs) belong to the shell temperature, and lower temperature portions are increased not only in the skin surface zone but also in the core zones. Depending on the season, the absolute skin temperatures of the torso, leg and extremities differ from each other immediately after bedtime. Also, the changes of skin temperature in accordance with the shift from the waking period to the deep sleep period are seasonally dependent. However, the facial temperature (specifically the forehead temperature) decreases as the subject falls asleep. This is seasonally independent due to a fall of the set point of the temperature regulatory center in the brain, which reduces the metabolism during sleep. At the discriminator 15, control of the cooling/heating means is made on the basis of input information of the temperatures of the individual body parts as well as such information as the room temperature and the room humidity. Prior to SWS, the body temperatures will be regulated by the discriminator 15 controlled cooling/heating means to be equal to the skin temperature during SWS. The control signals from the discriminator 15 for the cooling/heating means are provided to an output means 27 for the whole room air conditioner and an output means 28 for regional cooling and heating.

Figure 14:
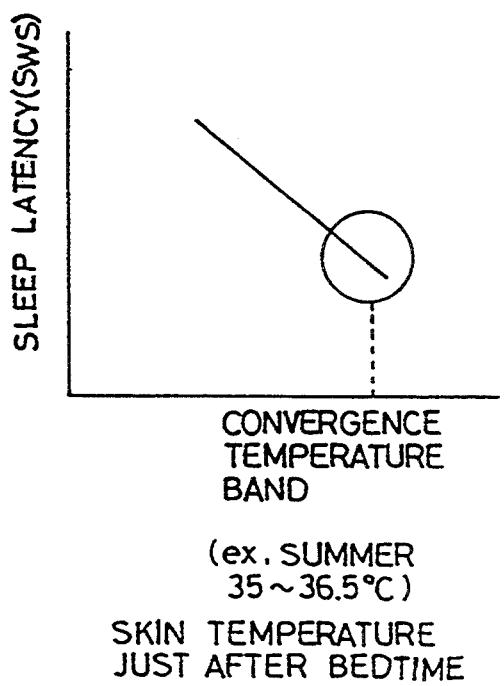
FIG. 14 is a diagram showing the relationship between the skin temperature immediately after going to bed and required time until the deep sleep is reached.

The cooling/heating means consist of a whole room air conditioner 40 and regional cooling and heating means 41. Research by the present inventors has revealed as shown in FIG. 14, that the required time for reaching the deep sleep can be reduced when the skin temperature, immediately after going to bed, is closer to the skin temperature during deep sleep. Therefore, the control signals to the whole room air conditioner 40 and regional cooling and heating means 41 are made so that the respective skin temperatures at the time of going to bed in the respective seasons will be the same as those during the deep sleep period as shown in FIG. 12, and the humidity in the room will be 50 to 65% of the relative humidity. In this case, the whole room air conditioner 40 may be any general air conditioners and for regional cooling and heating means 41, it will be possible to employ such devices as an electrical cooling pillow, an electric blanket, a water bed having an adjustable temperature, and radiative means for heating and cooling the head.

Figure 15:
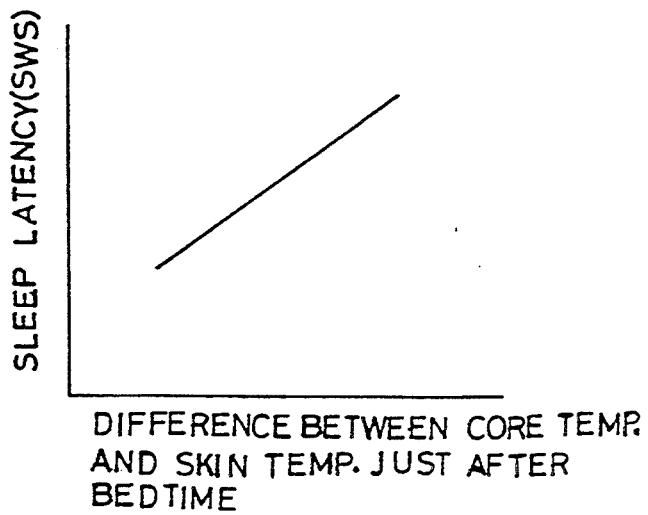
FIG. 15 is a diagram showing the relationship between the core temperature and the skin temperature.

A reduction of the time from bedtime to deep sleep is desired; therefore, from FIG. 15 which shows that the difference between core and skin temperatures is highly correlated to sleep latency, the difference between core and skin temperatures must be minimized. Thus, if core and skin temperatures are similar, heat removal inside the body will be minimized. In the embodiment, according to the present invention, as shown in FIG. 16, a core body temperature sensor 29 incorporating a thermistor, thermocouple or the like, is added to the embodiment of FIG. 11, so that an output signal of this core temperature sensor 29 is provided to a core temperature detector 30. The output signal of the core temperature detector 30 is connected to the discriminator 15, together with the output signals from the skin temperature detector 12, the room temperature detector 14, and the humidity detector 26. The temperature control mode is determined by the discriminator 15 on the basis of the information obtained from these signals. When, for example, both the core and skin temperatures are high, the whole room is slightly cooled so as not to overly decrease the leg temperature (specifically the thigh temperature), while cooling the face (specifically the forehead). The whole room air conditioning output means 27 and regional cooling and heating output means 28 receive a falling mode control signal from the discriminator 15.

Figure 17:
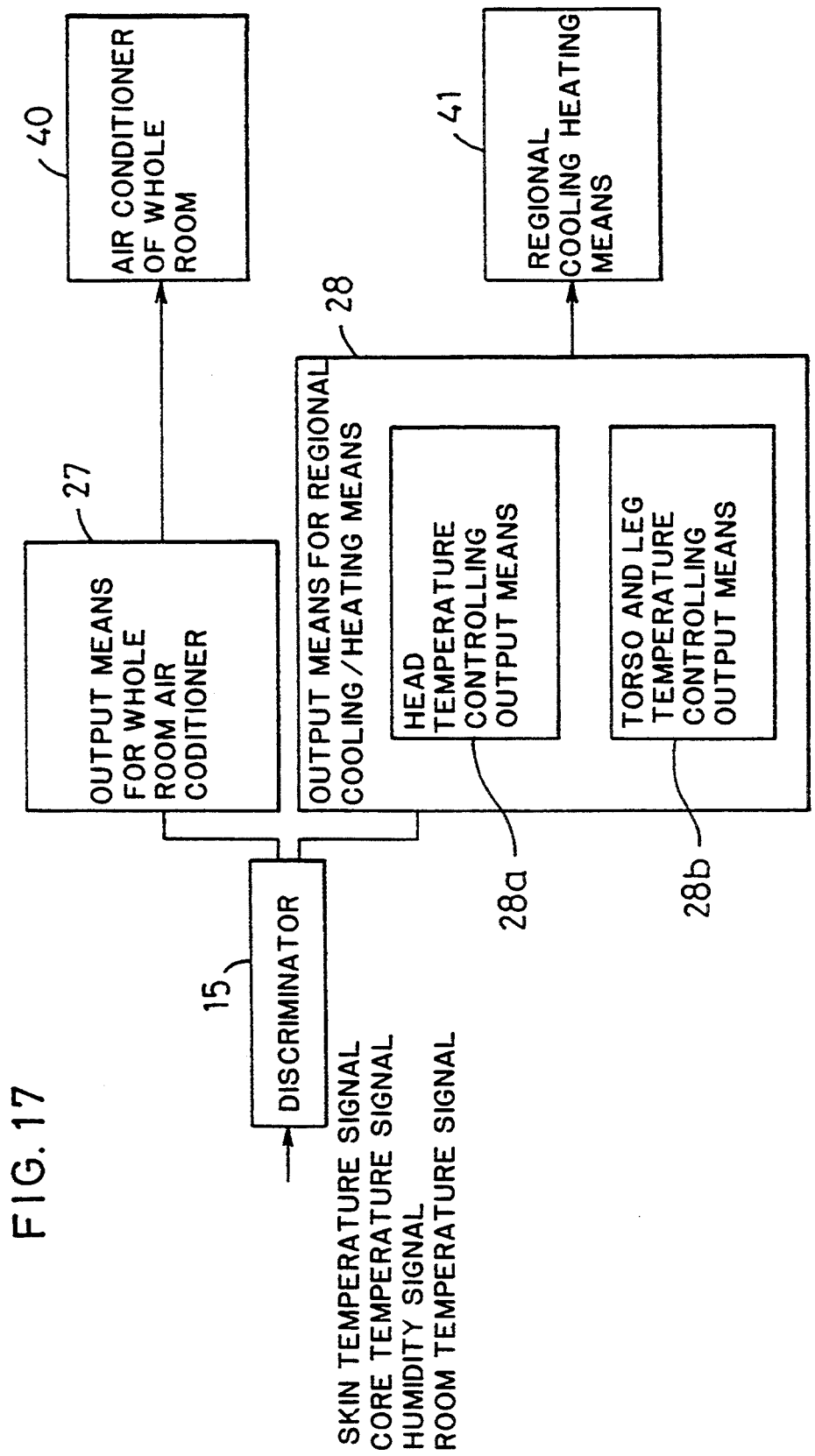

In another embodiment shown in FIG. 17, the same constituents as those in FIG. 1 are denoted by the same reference numerals.

In the embodiment shown in FIG. 17, the regional cooling and heating output means 28 includes a head temperature controlling output means 28a and a torso and leg temperature controlling output means 28b, and is arranged as to show three operating states, in accordance with the type of regional cooling and heating means 41. The head temperature controlling output means 28a only may be driven, the torso and leg temperature controlling output means 28b only may be driven, or both of the temperature controlling output means 28a and 28b may be driven. In summer, for example, a whole room air conditioner means 40 for controlling room temperature and humidity, and an electric cooling pillow for cooling the head (regional cooling and heating) are employed. It is possible to employ a water bed, or the like as the regional cooling and heating means 41 capable of controlling the temperature with a signal provided from the torso and leg temperature controlling output means 28b to attain the proper control of the skin temperatures below the neck.

Further, as shown in FIGS. 12 and 13, the body temperatures (including core and skin) show a remarkable seasonal difference, and the extent in which falling asleep can be aided varies depending upon the season. According to the present embodiment, therefore, the temperature regulating means is controlled so that the user's body temperature will be made closer to the basal temperature or a temperature during the SWS. More specifically, for example, the skin temperature of a user with an average temperature of 36.5° C. will be controlled as shown in the following TABLE:

TABLE

| Season | Facial Temp. (specif. forehead) | Torso and Arm Temp. | Leg Temp. (specif. thigh) |
|---|---|---|---|
| Summer | to 36.5° C. approx. lower by 0.5° C. than immed. before going to bed. | approx. 35 to 36.5° C. | greater than approx. 35° C. |
| Winter | 30 to 33° C. lower by approx. 0.5° C. than immed. before going to bed. | approx. 34 to 36° C. | greater than approx. 35° C. |

In order to aid the falling asleep more effectively, it is preferable that the leg temperature (specifically the thigh temperature) is made, in summer, to be above 35° C. and 0.5° to 1° C. higher than the facial temperature, and in winter, to be above 35° C. and 1° to 2° C. higher than the facial temperature (specifically the forehead temperature).

In the final embodiment, the same constituents as those in the embodiments of FIG. 1 and 9 are denoted by the same reference numerals.

Figure 18:
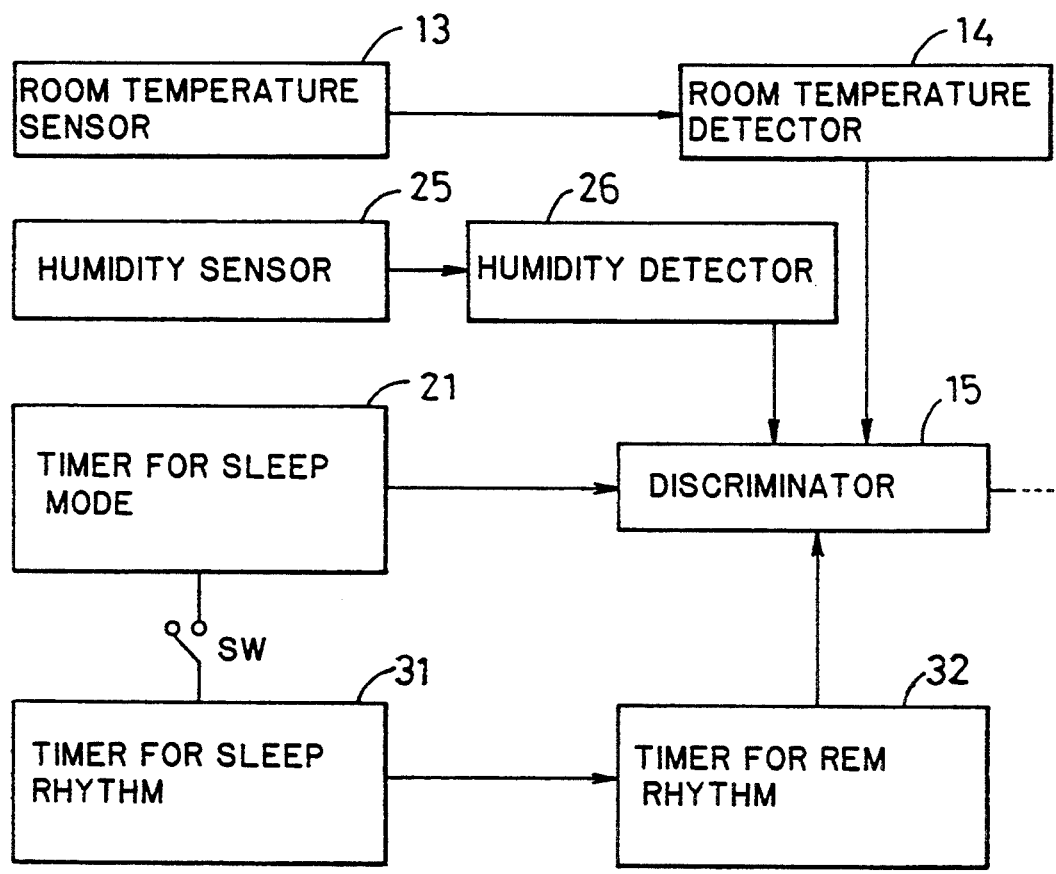

The final embodiment of the present invention is shown in FIG. 18. It is identical to the foregoing embodiment of FIG. 9, except for the additional provision of a humidity sensor 25 and humidity detector 26. The sleep rhythm timer 31 is actuated by the action of the switch SW after the sleep mode timer 21 is actuated and the initial temperature reaches a steady-state condition. The humidity is slightly decreased in the shallow sleep period mainly after the second cycle, but is gradually increased from deep sleep to the terminating stage of the REM period. While the onset time of the REM sleep deviates slightly from day to day as shown in FIG. 8 as has been partly described but, with the use of the REM rhythm timer, the phase difference of every day can be compensated for so as to be able to substantially remove this phase difference.

Figure 21:
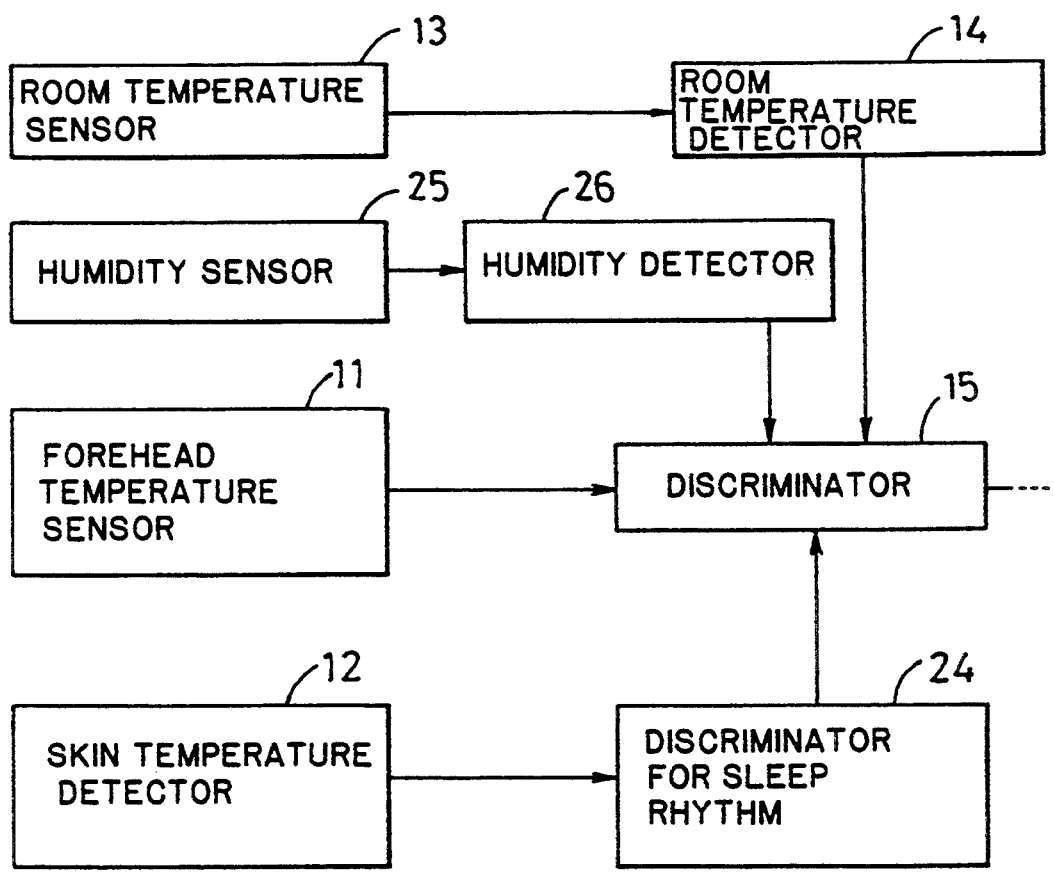
FIG. 21 is a block diagram showing still another embodiment of the present invention.

It has been further discovered that the facial temperature (specifically the forehead temperature) and the sleep depth have a relationship as shown in FIG. 12. As is clear from the illustrations, with deeper sleep, there is a decrease in forehead temperature. Thus, they are highly correlated having similar rhythms. While the facial temperature causes a phase deviation of approximately 10 to 20 minutes to occur with respect to the sleep rhythm, it is usefull for a sound sleep to compensate for such phase deviation. Further as will be clear when FIG. 21 is referred to, the same constituents as those in the embodiments of FIGS. 1 and 10 are denoted by the same reference numerals, this another embodiment is similar to the embodiment of FIG. 10 except for additional provision of the humidity sensor 25 and humidity detector 26. According to this arrangement, the sleep rhythm is calculated and determined from the forehead temperature by the sleep rhythm discriminator 24. The discriminator output signal controls such temperature regulating means as the whole room air conditioner, regional cooling and heating means, etc.

What is claimed is:

1. A system for regulating a user's body temperature for assuring smooth and good sleep of the user, the system comprising:
means for sensing the body temperature of the user in an objective region of the system, means for detecting from said body temperature a skin temperature of the user, means for detecting a room temperature in the objective region, means for discriminating a required control mode for attaining a regulated temperature through selected one of a plurality of temperature patterns in the objective region in response to outputs from said skin temperature detecting means and said room temperature detecting means, an output means for providing a control signal on the basis of said control mode discriminated at said discriminating means, and means for regulating said room temperature at said objective region in accordance with said control signal from said output means, wherein said room temperature detecting means includes a memory and a first timer, said memory storing data for monitoring variation with time in said room temperature for a first period determined by said first timer prior to the user's bedtime, and said body temperature sensing means includes a sensor for detecting the presence and absence of the user within said objective region during said first period.

2. The system according to claim 1, further comprising a timer means including a second timer for determining a second period after said bedtime to be variable, between about 20 to 30 minutes and about 1 hour dependent on said temperature pattern selected, said room temperature regulating means being actuated during said second period to raise the room temperature selectively quickly or slowly by, e.g., about 1° to 2° C. when the user's body temperature is about 36.5° C. to obtain a steady condition in the objective region.

3. The system according to claim 1, further comprising a second time for determining a second period after said bedtime to be variable dependent on said temperature pattern selected and in which the room temperature is selectively quickly or slowly increased to attain a steady temperature condition in the objective region, a third timer actuated when said steady temperature condition is reached for determining a third period following said second period and in which sleep rhythm is monitored to synchronize said temperature regulating means therewith, and a fourth timer connected to said discriminating means and said third timer for causing a phase delay to occur in REM rhythm included in said sleep rhythm and thus removing any day-to-day deviation in said REM rhythm.

4. The system according to claim 1, further comprising a facial temperature sensor, and a sleep discriminating means which calculates and determines a sleep cycle on the basis of an output signal of said facial temperature sensor.

5. The system according to claim 1, wherein said discriminating means includes a body temperature converging means for controlling a device giving an influence on respective temperatures at respective parts of the human body so as to shorten required time for converging the respective temperatures at respective body parts to a basal temperature obtained as substantially identical body temperature at any part in a deep sleep state.

6. The system according to claim 5, wherein said discriminating means further includes means for controlling a leg temperature specifically at a thigh part of the user to be close to said basal temperature.

7. The system according to claim 5, wherein said discriminating means further includes means for controlling a facial temperature specifically at a forehead part of the user to be close to said basal temperature.

8. The system according to claim 1, wherein said temperature regulating means includes means for cooling and heating the user's regional body part, and said discriminating means determines a control mode for regulating said regional body part cooling and heating means.

9. The system according to claim 1, wherein said body temperature sensing means includes a sensor for detecting core temperature, said temperature regulating means includes a whole room air conditioning means and a regional body part cooling and heating means, and said discriminating means includes means for determining a control mode for said temperature regulation, including said whole room air conditioning means and regional body part cooling and heating means in accordance with said core temperature provided from said sensor.

10. The system according to claim 8, wherein said control mode for said regional body part cooling and heating means includes a mode for regionally cooling and heating the user's legs specifically at thigh parts.

11. The system according to claim 8, wherein said control mode for said regional body part cooling and heating means includes a mode for regionally cooling and heating the user's face specifically at forehead part.

12. The system according to claim 8, wherein said control mode for said regional body part cooling and heating means includes a first mode for regionally cooling and heating the the user's legs specifically at thigh parts, and a second mode for regionally cooling and heating the user's face specifically at forehead part.

13. The system according to claim 1, wherein said control mode of said discriminating means includes a mode for rendering, in summer, a facial temperature specifically at forehead part to be slightly lower, by about 0.5° to 1° C., than that immediately before going to bed but to be within a range of about 35° to 36.5° C. of a basal temperature obtained as substantially identical body temperature at any art in deep sleep state, the skin temperature of the user's torso including arms to be within the range of the basal temperature, and a skin temperature of the legs specifically at the thigh parts to be higher than the basal temperature.

14. The system according to claim 1, wherein said control mode of said discriminating means includes modes for rendering, in winter and late autumn, a facial temperature specifically at the user's forehead to be slightly lower by about 0.5° to 1° C., than that immediately before going to bed but to be much lower, by about 3° to 5° C. than a basal temperature obtained as substantially identical body temperature at any body part in deep sleep state, a skin temperature at the user's torso including arms to be within a range of about 34° to 36° C. of the basal temperature, and another skin temperature at the legs specifically at high parts to be higher than the basal temperature.

15. The system according to claim 1, wherein said control mode of said discriminating means includes a mode for rendering, in summer, a skin temperature of the user's legs specifically at thigh parts to be slightly higher by about 0.5° to 1.5° C., than a facial temperature specifically at forehead part of the user.

16. The system according to claim 1, wherein said control mode of said discriminating means includes a mode for rendering, in winder and late autumn, a skin temperature of the the user's legs specifically at thigh parts to be higher, by about 1° to 2° C., than a facial temperature specifically at forehead part of the user.

17. The system according to claim 1, which further comprises a humidity sensor provided with respect to said objective region, and said discriminating means determines said control mode in accordance with the output from said humidity sensor in addition to detection outputs of said skin temperature and room temperature detecting means.

* * * * *